Aug. 26, 1958 A. E. LANG Plant Pat. 1,745
STRAWBERRY PLANT
Filed April 2, 1957 2 Sheets-Sheet 1
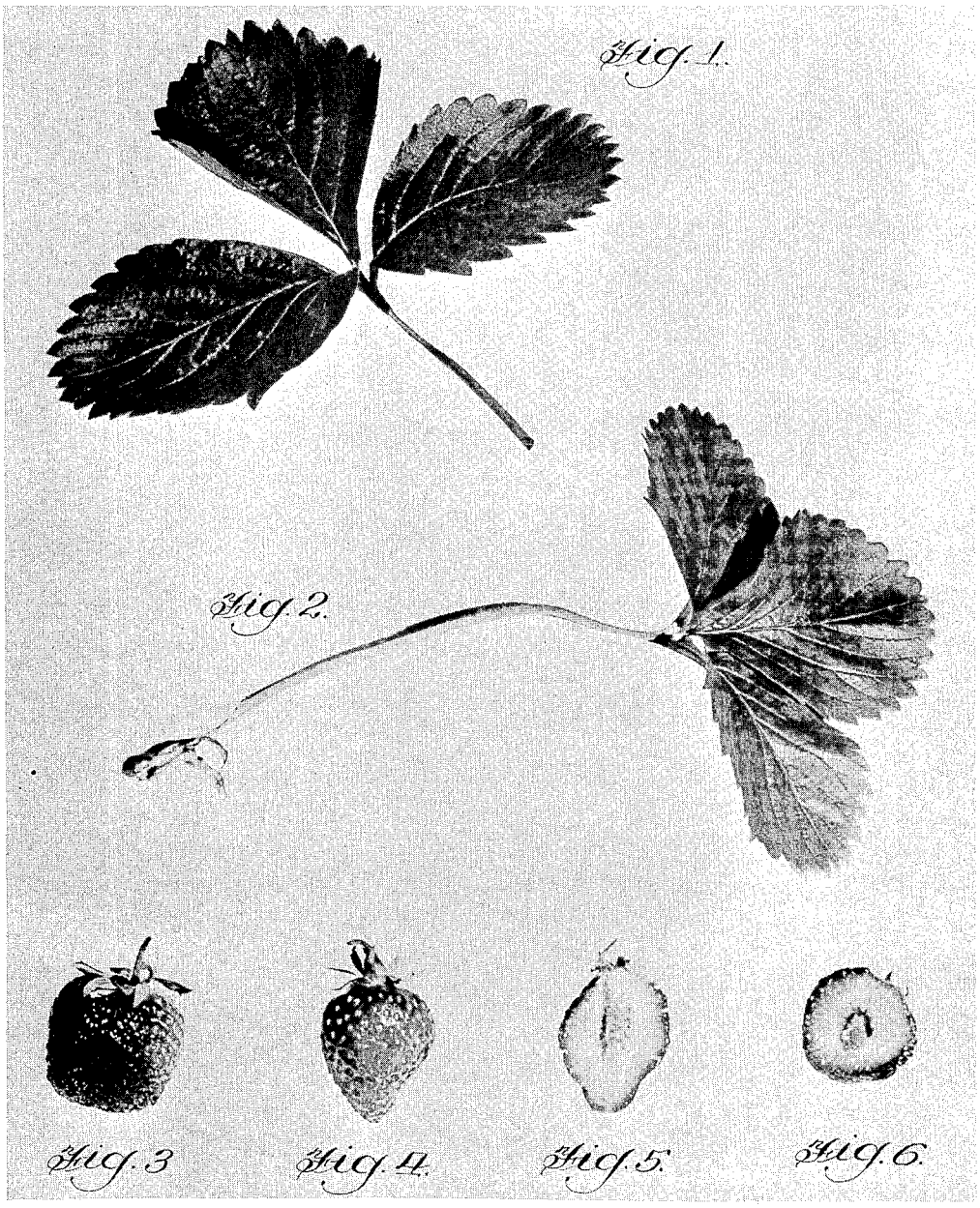
Inventor
Albin E. Lang
By L. F. Hammond
Attorney STRAWBERRY PLANT
Filed April 2, 1957 2 Sheets-Sheet 2
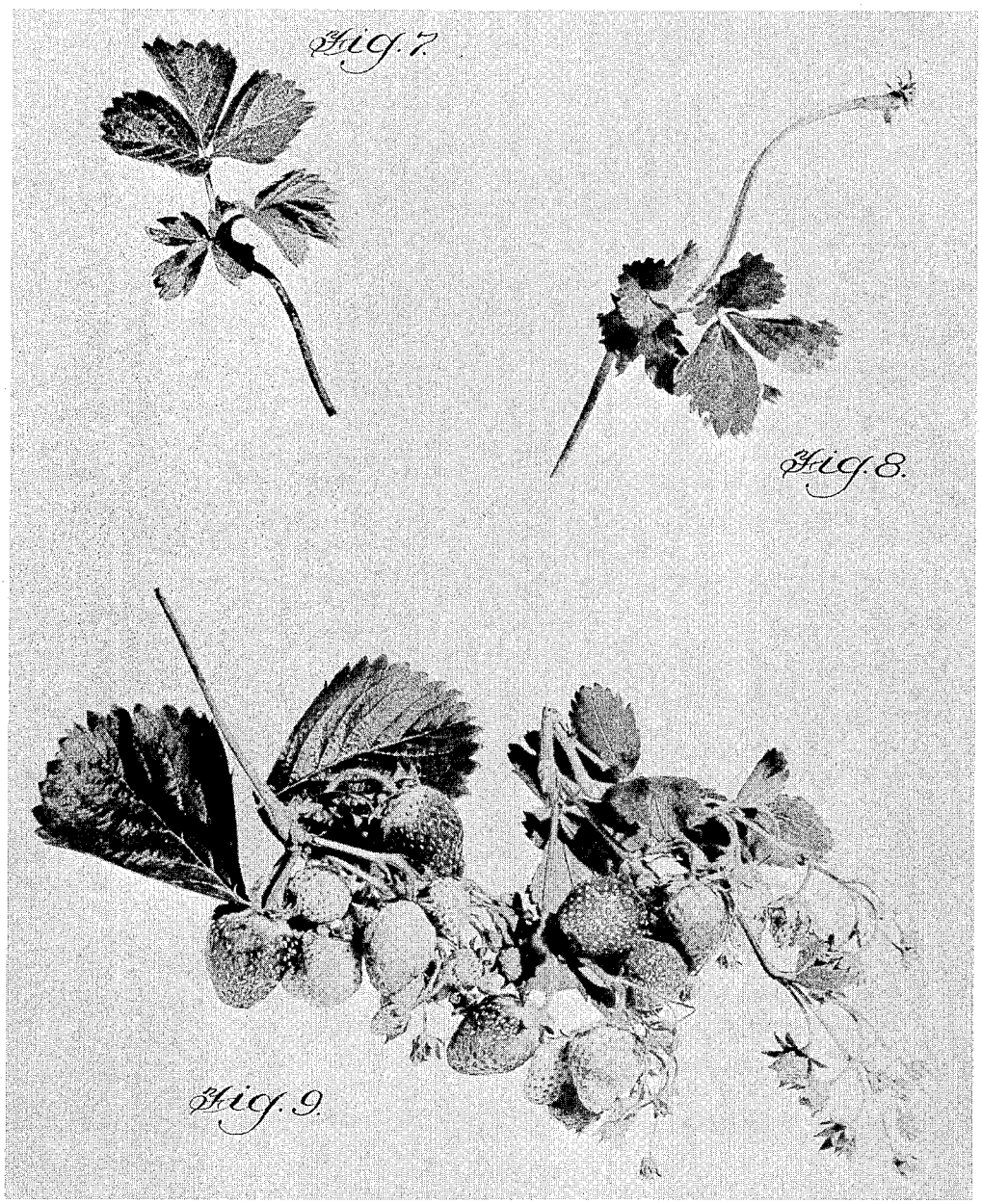
Inventor
Albin E. Lang
By L. F. Hammond
Attorney United States Patent Office Plant Pat. 1,745
Patented Aug. 26, 1958

1,745

STRAWBERRY PLANT

Albin E. Lang, Dodgeville, Wis.

Application April 2, 1957, Serial No. 650,285

1 Claim. (Cl. 47—62)

My invention relates to a new and distinct variety of strawberry plant. This new and distinct variety is the result of deliberate self-pollination, under carefully safeguarded conditions to prevent any open pollination, of the all-summer bearing strawberry plant which is the subject of Plant Patent No. 1,408 issued to me August 2, 1955. (The plant of said Plant Patent No. 1,408 is sold under the name "Esteem.")

The self-pollination of an "Esteem" plant occurred on July 28, 1951; and several fully developed berries resulted from the inbreeding. Seeds from these berries were planted by me in October 1951. Approximately 300 seedlings developed the following spring and summer from such seed; and were transplanted by me in July of that year, 1952, in my garden in the city of Platteville, Grant County, Wisconsin. In July of 1953 the subject variety was selected from the inbred seedlings, above described; and all other plants were destroyed. By crown division and by the transplanting of rooted runners, in my said garden, I asexually reproduced by October of 1953, approximately 50 plants of the new variety, thus enabling me thoroughly to study the new and distinct characteristics of the new plant and to observe the permanence of such characteristics.

The studies continued during the spring, summer, and fall of 1954.

In October of 1954, approximately 500 of the best runner plants were transplanted in my new garden in the city of Dodgeville, in Iowa County, Wisconsin. All of the subject plants not transplanted were carefully destroyed.

A further study of the plants and further asexual reproduction of them in my new garden, convinced me of unique and new features, and of the persistence thereof through successive generations of asexual reproduction.

Generally the new and unique characteristics are the heavy production of runners; the extended production of fruit until well after the first so-called "killing" frost; and the resistance to extremes of temperature and to the most common (in this area) diseases and pests.

Each successive generation of plants has the same distinctively unique characteristics which were exhibited by the original inbred seedlings, with the result that there has been developed a new and distinct variety of strawberry plant embodying desirable qualities not known heretofore.

In the accompanying illustrations Figures 1 and 2 are typical leaves. Figures 3 and 4 are typically shaped berries. Figures 5 and 6 are respectively longitudinal and transverse cross sections through median lines of typical berries. Figures 7 and 8 are typical runner tips, that in Figure 7 being the more mature.

Finally, Figure 9 illustrates two typical berry clusters picked in the open garden on October 1, 1956, and photographed that day. Other berry clusters were picked from the same garden, and from the same or similar plants, and exhibited at a convention of berry growers on November 9, 1956, a plurality of weeks after strawberry plants of other varieties in my garden and elsewhere in the area (approx. 43° N., 90° W., elevation 1200′) had been killed by frost.

I now refer in detail to the unique characteristics and qualities of my new variety of strawberry plant, which in combination distinguish it readily from all other known varieties.

The subject plant is an everbearer. One of its most unique and valuable features is the prolific production of runners, primary, secondary, and tertiary. (By these terms I mean that a first or primary runner shoot roots; it, in turn, sends out a secondary runner, which roots; and the secondary runner, in the course of a single growing season, will put forth a third (tertiary) runner.) To be concrete, the average number of rooted runners from a single plant from early May 1956 until September of the same year is fifty; and many mother plants in the same period produced more than seventy rooted runners.

Another unique quality, coupled with the sturdy prolific runners, is that both the primary and secondary runners produce fruit before the plant is frost-killed. Runner production from plants newly set out in the spring starts in about three weeks. Blossoms appear on the mother plant late in June, and later on the primary and secondary runner plants.

On plants a year old blossoming begins about May 10. Fruit is borne through an average June bearing season of slightly over two weeks. Blossoms appear again in late June on the mother plant, in July on the primary runners, and still later on the secondary runners. The bearing load is first carried by the mother plant, next by the primary runner plants, and finally by the secondary runner plants.

The foliage is extremely vigorous, and thick, but not rank. I account for the fact that late fall fruit is not harmed by frost by the feature that the berry cluster is so thoroughly covered by the leaves. This also serves to prevent sun damage to the berries; and, by shade, to conserve moisture in the surface soil.

The general characteristics of the fruit are as follows: The berries have a rich, mildly acid, tangy flavor, which somewhat resembles that of the northern wild strawberry, fragaria virginiana. The flesh is relatively firm and of good durability. The berry is somewhat larger than the "Esteem" berry of Plant Patent 1,408; but much the same shape, being generally conical with a rounded nose. Like "Esteem," it is relatively smooth. The berry is a rich, dark red on the surface; and shows a tendency toward white under the calyx and on the inside. The core is relatively small. The surface of the berry is lustrous. The seeds are flush with the surface.

Additional characteristics appear in the following tabulation:

*Plant characteristics*

*Size.*—Large, wide-spreading rows.

*Crown.*—About three-eighths inch thick by an inch in length.

*Leaves.*—Extremely dark green in color; lighter underneath.

*Leaflets.*—Three. Regularly serrated margins. Terminal leaflet relatively blunt compared with uniformly rounded tip of "Esteem." Only slightly cupped and overlapping.

*Petiole.*—Somewhat longer than "Esteem," but not as heavy or rigid.

*Flower stem.*—Thick, heavy, medium pubescense. Seldom upright. Seldom exposed.

*Runners.*—Hardy and freely produced. Many produce blossoms while rooting. Primary and secondary runners produce fruit the season of their appearance.

*Flower.*—Large, perfect, self-pollinating. Most blossoms produce a marketable berry.

*Heat and drought resistance.*—Good because of sturdy root system and protective mat of leaves covering berry clusters and top soil.

*Roots.*—Medium in size, average length. Less fibrous than "Esteem." Very sturdy.

*Fruit*

*Size.*—Range from 2.5" to 5" in circumference, and from 1" to 2.25" long. Invariably all of marketable size. Larger than "Esteem."

*Shape.*—Conical with rounded nose.

*Aspect.*—Glossy.

*Color.*—Uniformly dark red, white under calyx.

*Seeds.*—Yellow achenes when ripe. Flush with surface.

*Calyx.*—Does not lie flat against top of berry when latter is ripe.

*Flesh.*—Fine texture, firm, quite juicy.

*Flavor.*—Tangy, wild flavor, rich.

*Keeping quality.*—Exceptionally good.

*Uses.*—Recommended for canning and freezing.

The plant above described may vary in degree from the typical features above set forth, depending on soil, climate, and weather; but the plant has been grown experimentally in States adjoining Wisconsin and no noticeable difference has been observed in distinguishing characteristics.

What I claim is:

A new and distinct variety of strawberry substantially as herein shown and described, characterized by its persistent habit of heavy runner production; the production of fruit on both primary and secondary runner plants in the season of their appearance; its resistance to frost; and the everbearing production of large, tangy-flavored berries.

References Cited in the file of this patent

Publication: Catalog—Benton County Nursery Co., Inc., Rogers, Arkansas. Spring 1956 (Description of Ozark Beauty Strawberry Plant).